United States Patent
Patel et al.

(10) Patent No.: US 10,058,113 B2
(45) Date of Patent: *Aug. 28, 2018

(54) SHELF-STABLE, CLEAR LIQUID NUTRITIONAL COMPOSITIONS COMPRISING EPIGALLOCATECHIN GALLATE (EGCG) AND METHODS FOR PREPARING THE SAME

(71) Applicant: ABBOTT LABORATORIES, Abbott Park, IL (US)

(72) Inventors: Guarav Patel, Gahanna, OH (US); Paul Johns, Columbus, OH (US); Normanella Dewille, Columbus, OH (US); Suzette Pereira, Westerville, OH (US)

(73) Assignee: ABBOTT LABORATORIES, Abbott Park, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/588,950

(22) Filed: May 8, 2017

(65) Prior Publication Data

US 2017/0238583 A1   Aug. 24, 2017

Related U.S. Application Data

(63) Continuation of application No. 14/432,015, filed as application No. PCT/US2013/063394 on Oct. 4, 2013, now Pat. No. 9,675,097.

(60) Provisional application No. 61/709,715, filed on Oct. 4, 2012, provisional application No. 61/781,681, filed on Mar. 14, 2013.

(51) Int. Cl.
| | |
|---|---|
| *A23L 3/00* | (2006.01) |
| *A23L 2/52* | (2006.01) |
| *A23L 2/46* | (2006.01) |
| *A23L 2/66* | (2006.01) |

(52) U.S. Cl.
CPC ........ *A23L 2/52* (2013.01); *A23L 2/46* (2013.01); *A23L 2/66* (2013.01); *A23V 2002/00* (2013.01)

(58) Field of Classification Search
CPC .................................. A23L 2/66; A23K 36/82
USPC ................... 426/590, 597, 648, 634, 583
See application file for complete search history.

(56) References Cited

U.S. PATENT DOCUMENTS

| | | |
|---|---|---|
| 2006/0188548 A1 | 8/2006 | Mattson et al. |
| 2008/0193601 A1 | 8/2008 | Nasser |
| 2009/0035440 A1 | 2/2009 | Velikov |
| 2011/0021421 A1 | 1/2011 | Kiers et al. |
| 2011/0305799 A1 | 12/2011 | Dewille et al. |
| 2012/0093933 A1* | 4/2012 | Livney et al. |

FOREIGN PATENT DOCUMENTS

WO    2012/097061 A1    7/2012

OTHER PUBLICATIONS

Shelf-Stable Clear Liquid Nutritional Compositions Comprising Epigallocatechin Gallate (EGCg) and Methods for Preparing the Same, First Office Action in China after entering nationalization stage for related application No. 201380063234.4, 10 pages (May 10, 2016).
Sahelian, R., EGCG green tea extract health benefit, side effects, effect on metabolism, cancer protection or treatment, does it work for weight loss?, http://www.raysahelian.com/egcg.html, p. 1-7 (Jun. 20, 2015).
Shpigelman et al., Thermally-induced protein-polyphenol co-assemblies: beta lactoglobulin-based nanocomplexes as protective nanovehicles for EGCG, Food Hydrocolloids, 24:8 p. 735-743 (Nov.-Dec. 2010).
European Search report dated Aug. 10, 2017 from corresponding European Application No. 17172624.3.
Written Opinion dated Aug. 10, 2017 from corresponding Application No. PCT/US2013/063394.
Shelf-Stable Clear Liquid Nutritional Compositions Comprising Epigallocatechin Gallate (EGCg) and Methods for Preparing the Same, First Office Action in China after entering nationalization stage for related application No. 201380063234.4, May 10, 2016, 10 pages.

* cited by examiner

*Primary Examiner* — Helen F Heggestad

(57) ABSTRACT

Disclosed herein are shelf-stable, clear liquid nutritional compositions having a pH ranging from 2.5 to 4.6 and comprising water; at least one source of EGCg in an amount sufficient to provide 200-1700 mg/L of EGCg; and at least one source of protein in an amount sufficient to provide 25-45 g/L of total protein. The shelf-stable, clear liquid nutritional compositions lose no more than 20% by weight solids of the EGCg content present in the initial formulation of the compositions to epimerization, degradation, or both epimerization and degradation during heat sterilization. In certain embodiments, the loss of EGCg is exhibited by the amount of epimerization product GCg present in the shelf-stable, clear liquid nutritional composition following heat sterilization. Methods for preparing the shelf-stable, clear liquid nutritional compositions are also disclosed herein.

26 Claims, No Drawings

SHELF-STABLE, CLEAR LIQUID NUTRITIONAL COMPOSITIONS COMPRISING EPIGALLOCATECHIN GALLATE (EGCG) AND METHODS FOR PREPARING THE SAME

CROSS REFERENCE TO RELATED APPLICATIONS

This application is a continuation application of U.S. Non-Provisional application Ser. No. 14/432,015, filed Mar. 27, 2015, now U.S. Pat. No. 9,675,097, which is the U.S. national stage entry of PCT/US2013/063394, with an international filing date of Oct. 4, 2013, which claims priority to and any benefit of U.S. Provisional Application No. 61/709,715, filed Oct. 4, 2012 and U.S. Provisional Application No. 61/781,681, filed Mar. 14, 2013, the entire contents of which are incorporated by reference in their entirety.

FIELD OF THE DISCLOSURE

The present disclosure relates to shelf-stable, clear liquid nutritional compositions comprising epigallocatechin gallate ("EGCg") and methods for preparing the shelf-stable, clear liquid nutritional compositions.

BACKGROUND

Consumers can improve their overall health and well-being by consuming nutritional products containing a balance of protein, carbohydrates, vitamins, minerals, and other nutrients. Shelf-stable liquid nutritional compositions are a popular form of such nutritional products. Shelf-stable products are generally prepared and packaged in a manner that extends the shelf-life of the product and that also allows the packaged product to be safely stored at room or ambient temperature for long durations (e.g., more than twelve months).

The nutritional products are often formulated with certain active ingredients that help tailor the product to a specific therapeutic or nutritional benefit. Epigallocatechin gallate, also known as EGCg (or epigallocatechin 3-gallate), has been identified as one such beneficial active ingredient. However, the EGCg present in certain protein-containing liquid nutritional compositions can be sensitive to preparation techniques involving high temperatures, such as aseptic or retort sterilization techniques, generally used to obtain the shelf-stable product. EGCg present in these certain compositions will epimerize, chemically degrade (e.g., hydrolyze or oxidize), or both epimerize and chemically degrade when subjected to the high temperatures generally associated with aseptic or retort sterilization.

SUMMARY

Disclosed herein are shelf-stable, clear liquid nutritional compositions and methods for preparing the shelf-stable, clear liquid nutritional compositions. Embodiments of the shelf-stable, clear liquid nutritional compositions are sterilized or stabilized and have a pH ranging from 2.5 to 4.6. The shelf-stable, clear liquid nutritional compositions include water, a source of EGCg, and a source of protein. The shelf-stability of the composition is exhibited by the lack of epimerization and degradation products of the EGCg present in the sterilized composition. In particular, the shelf-stable, clear liquid nutritional products disclosed herein lose no more than 20% by weight solids of the EGCg content present in the initial formulation of the composition to epimerization, degradation, or both epimerization and degradation during heat sterilization. In certain embodiments, the loss of EGCg is exhibited by the amount of epimerization product gallocatechin gallate ("GCg") present in the composition following heat sterilization.

In accordance with certain embodiments of the shelf-stable, clear liquid nutritional compositions disclosed herein, a sterilized, clear liquid nutritional composition is provided. The composition comprises water; at least one source of EGCg in an amount sufficient to provide 200-1700 mg/L of EGCg (in the sterilized, clear liquid nutritional composition); and at least one source of protein in an amount sufficient to provide 25-45 g/L of total protein (in the sterilized, clear liquid nutritional composition). The pH of the composition ranges from 2.5 to 4.6. The composition contains no more than 340 mg/L of GCg and is clear after sterilization.

In another embodiment, a method for preparing a sterilized, clear liquid nutritional composition is provided. The method comprises heating an unsterilized liquid nutritional composition having a pH ranging from 2.5 to 4.6 to a temperature ranging from 85° C. (185° F.) to 152° C. (306° F.) for a period of time sufficient to produce a sterilized liquid nutritional composition. The sterilized liquid nutritional composition comprises water; at least one source of EGCg in an amount sufficient to provide 200-1700 mg/L of EGCg (in the sterilized, clear liquid nutritional composition); and at least one source of protein in an amount sufficient to provide 25-45 g/L of total protein (in the sterilized, clear liquid nutritional composition). The sterilized liquid nutritional composition contains no more than 340 mg/L of GCg.

In another embodiment, a method for preparing a sterilized, clear liquid nutritional composition is provided. The method comprises admixing at least one source of epigallocatechin gallate (EGCg) and at least one source of whey-based protein containing β-lactoglobulin to form an admixture, where the admixture comprises EGCg and β-lactoglobulin in amounts sufficient to provide a molar ratio of EGCg to β-lactoglobulin of 1:1 to 11:1 in the admixture. The admixing occurs at a pH of 2.5 to 4.6. The method also includes a step directed to forming an unsterilized liquid nutritional composition by combining the admixture with at least one of the following ingredients: water; an additional source of EGCg; and an additional source of protein selected from the group consisting of whey-based proteins, acidified soy protein isolates, soy protein hydrolysates, casein hydrolysates, pea hydrolysates, and combinations thereof. In addition, the method includes the steps of adjusting the pH of the unsterilized nutritional composition to obtain a pH ranging from 2.5 to 4.6, if necessary, and heating the unsterilized liquid nutritional composition to a temperature ranging from 85° C. (185° F.) to 152° C. (306° F.) for a period of time sufficient to produce a sterilized liquid nutritional composition. The sterilized nutritional composition produced according to this method comprises water, 200-1700 mg/L of total EGCg, 25-45 g/L of total protein, and no more than 340 mg/L of gallocatechin gallate (GCg).

In another embodiment, a stabilized, clear liquid nutritional composition is provided. The composition comprises water; at least one source of EGCg in an amount sufficient to provide 200-1700 mg/L of an initial amount of EGCg; and at least one source of protein in an amount sufficient to provide 25-45 g/L of total protein. The at least one source of protein comprises β-lactoglobulin in an amount sufficient to provide a molar ratio of EGCg to β-lactoglobulin of 1:1 to 11:1 in the composition. The pH of the composition ranges from 2.5 to 4.6. The liquid nutritional composition is sufficiently stable such that it will lose no more than 20% by weight solids of the initial amount of EGCg in the liquid nutritional composition if heated to a temperature ranging from 85° C. (185° F.) to 152° C. (306° F.) for period of time sufficient to sterilize the composition.

DETAILED DESCRIPTION

Disclosed herein are shelf-stable, clear liquid nutritional compositions having a pH ranging from 2.5 to 4.6 and comprising water; at least one source of EGCg in an amount sufficient to provide 200-1700 mg/L of EGCg; and at least one source of protein in an amount sufficient to provide 25-45 g/L of total protein. The shelf-stable, clear liquid nutritional compositions lose no more than 20% by weight solids of the EGCg content present in the initial formulation of the compositions to epimerization, degradation, or both epimerization and degradation during heat sterilization. In certain embodiments, the loss of EGCg is exhibited by the amount of epimerization product GCg present in the shelf-stable, clear liquid nutritional composition following heat sterilization. Methods for preparing the shelf-stable, clear liquid nutritional compositions are also disclosed herein.

As used herein, "shelf-stable" refers to a sterilized product or a stabilized product. The term "sterilized" as used herein refers to a composition or product that has been treated in a manner to kill the microorganisms in the composition that are capable of growth such that it can be stored at room or ambient temperature for long durations, e.g., more than twelve months, and still be safely consumed. In certain embodiments, the shelf-stable, clear liquid nutritional compositions disclosed herein are heat sterilized using techniques including, but not limited to aseptic sterilization, retort sterilization, hot-fill sterilization, and the like. No more than 20% by weight solids of the initial EGCg content present in the formulation of the liquid nutritional compositions disclosed herein is lost to epimerization, degradation, or both epimerization and degradation during heat sterilization. In other words, heat sterilized, clear liquid nutritional compositions disclosed herein contain greater than 80% by weight solids of the initial amount of EGCg present in the finalized (i.e., no other ingredients are added) but unsterilized formulation of the composition, i.e., the amount present in the finalized composition before sterilization (solids are referred to herein so as to eliminate any solvent-type liquid from a liquid extract or any residual moisture from a solid-type extract). The sterilized, clear liquid nutritional compositions disclosed herein have a pH ranging from 2.5 to 4.6. In certain embodiments, the sterilized, clear liquid nutritional compositions disclosed herein have a pH ranging from 2.5 to 4. In certain embodiments, the sterilized, clear liquid nutritional compositions disclosed herein have a pH ranging from 2.5 to 3.5. In certain embodiments, the sterilized, clear liquid nutritional compositions disclosed herein have a pH ranging from 3 to 3.5.

In other embodiments, the shelf-stable, clear liquid nutritional compositions disclosed herein may be subject to other sterilization techniques, including but not limited to, chemical sterilization, pH sterilization, irradiation sterilization, pressure sterilization, filtration sterilization, or combinations thereof, as an alternative, or in addition to, heat sterilization. In accordance with this embodiment, whether another sterilization technique is used as an alternative or in addition to heat sterilization, the shelf-stable, clear liquid nutritional compositions disclosed herein would obtain the same results as described above as is the case if the compositions were heated sterilized, i.e., no more than 20% by weight solids of the initial EGCg content present in the formulation of the liquid nutritional compositions disclosed herein is lost to epimerization, degradation, or both epimerization and degradation during sterilization.

The term "stabilized" as used herein refers to a liquid nutritional composition disclosed herein prior to sterilization. More specifically, with respect to certain of the previously mentioned embodiments, a stabilized composition is an unsterilized composition that will, upon heat sterilization, lose no more than 20% by weight solids of the initial amount of EGCg present in the finalized, but unsterilized formulation of the composition. Thus, in other words, if it is heat sterilized, the stabilized, clear liquid nutritional compositions disclosed herein will contain greater than 80% by weight solids of the initial amount of EGCg present in the unsterilized composition. A stabilized composition includes, but is not limited to, an unsterilized shelf-stable, clear liquid nutritional composition that has a pH ranging from 2.5 to 4.6. In certain embodiments, the stabilized, clear liquid nutritional compositions disclosed herein have a pH ranging from 2.5 to 4. In certain of the preceding embodiments, the stabilized, clear liquid nutritional compositions disclosed herein have pH ranging from 2.5 to 3.5. In certain of the preceding embodiments, the stabilized, clear liquid nutritional compositions disclosed herein have pH ranging from 3 to 3.5. In the sterilized embodiments of the shelf-stable, clear liquid nutritional compositions disclosed herein, a sterilization process is applied to the stabilized, clear liquid nutritional composition to produce the sterilized, clear liquid nutritional composition.

In certain embodiments, the shelf-stable, clear liquid nutritional composition comprises a sterilized, clear liquid nutritional composition. The composition includes water; at least one source of EGCg in an amount sufficient to provide 200-1700 mg/L of EGCg; and at least one source of protein in an amount sufficient to provide 25-45 g/L of total protein. The pH of the composition ranges from 2.5 to 4.6. In certain of the preceding embodiments, the pH ranges from 2.5 to 4, the pH ranges from 2.5 to 3.5, or the pH ranges from 3 to 3.5. The composition contains no more than 340 mg/L of GCg and is clear after sterilization. Furthermore, in certain of the preceding embodiments, the at least one source of protein comprises β-lactoglobulin in an amount sufficient to provide a molar ratio of EGCg to β-lactoglobulin of 1:1 to 11:1 in the unsterilized composition. In other embodiments, the at least one source of protein comprises β-lactoglobulin in an amount sufficient to provide a molar ratio of EGCg to β-lactoglobulin of 1:1 to 9:1, and yet in other embodiments, the at least one source of protein comprises β-lactoglobulin in an amount sufficient to provide a molar ratio of EGCg to β-lactoglobulin of 1:1 to 7:1.

In certain embodiments, the shelf-stable, clear liquid nutritional composition comprises a stabilized, clear liquid nutritional composition. The composition includes water; at least one source of EGCg in an amount sufficient to provide 200-1700 mg/L of an initial amount of EGCg; and at least one source of protein in an amount sufficient to provide 25-45 g/L of total protein (in the stabilized, clear liquid nutritional composition). The pH of the composition ranges from 2.5 to 4.6. In certain of the preceding embodiments, the pH ranges from 2.5 to 4, the pH ranges from 2.5 to 3.5, or the pH ranges from 3 to 3.5. Furthermore, in certain of the preceding embodiments, the at least one source of protein comprises β-lactoglobulin in an amount sufficient to provide a molar ratio of EGCg to β-lactoglobulin of 1:1 to 11:1 in the stabilized composition, including a molar ratio of EGCg to β-lactoglobulin of 1:1 to 9:1, and including a molar ratio of EGCg to β-lactoglobulin of 1:1 to 7:1. The liquid nutritional composition is sufficiently stable such that it will lose no more than 20% by weight solids of the initial amount of EGCg in the liquid nutritional composition if heated to a temperature ranging from 85° C. (185° F.) to 152° C. (306° F.) for a period of time sufficient to sterilize the composition.

As previously discussed, the shelf-stable, clear liquid nutritional compositions disclosed herein include at least one source of EGCg in an amount sufficient to provide 200-1700 mg/L of EGCg. In accordance with certain of the preceding embodiments, the source of EGCg is present in an amount sufficient to provide 500-1525 mg/L of EGCg in the final composition (e.g., the sterilized composition). In addition, in accordance with certain of the preceding embodiments, the source of EGCg is present in an amount sufficient to provide 675-1525 mg/L of EGCg in the final composition. In certain of the preceding embodiments, the source of EGCg is present in an amount sufficient to provide 900-1350 mg/L of EGCg in the final composition.

EGCg is a polyphenol, specifically a catechin, that is desirable for many therapeutic and nutritional benefits. EGCg is the most abundant polyphenol present in green tea. Accordingly, suitable sources of EGCg for the shelf-stable, clear liquid nutritional compositions disclosed herein are green tea-based sources including, but not limited to, green tea extracts in which EGCg alone, or in combination with other polyphenol compounds, are isolated from green tea as an extract. Examples of such suitable green tea extracts are in the form of a liquid with a high concentration of the polyphenols, a solid (e.g., a powder), and mixtures thereof. In certain embodiments where green tea extract is utilized, the extract is decaffeinated such that it contains less than 1% by weight caffeine, or even less than 0.5% by weight caffeine. In addition to containing EGCg, suitable green tea extracts used with the shelf-stable, clear liquid nutritional compositions disclosed herein may contain other polyphenols including other catechins such as catechin (i.e., (+)-catechin, also known as "C"), epicatechin ("EC"), gallocatechin ("GC"), epigallocatechin ("EGC"), and epicatechin gallate ("ECg"); flavones such as apigenin, isoviloxin, sapotarin, and vicenin-2; flavonols such as kaempherol, quercetin, myricetin; condensed flavanoids, and tannin glycosides. Accordingly, in certain embodiments, in addition to EGCg, the at least one source of EGCg includes at least one of C, EC, GC, EGC, ECg, and combinations thereof. In certain embodiments, sources of EGCg other than green tea-based sources may be utilized. These sources include, but are not limited to, oolong tea-based sources such as oolong tea, oolong tea extracts, and the like; white tea-based sources such as white tea, white tea extracts, and the like; macha tea, macha tea extracts, and the like; yellow tea, yellow tea extracts, and the like; and dark tea (i.e., Chinese dark tea), dark tea extracts, and the like.

In certain embodiments, the at least one source of EGCg contains at least 30% of EGCg by weight solids of the at least one source of EGCg. In accordance with certain of the preceding embodiments, the at least one source of EGCg contains at least 45% of EGCg by weight solids of the at least one source of EGCg. In one embodiment, the at least one source of EGCg contains 30-100% of EGCg by weight solids of the at least one source of EGCg. In certain embodiments, the at least one source of EGCg contains 45-100% of EGCg by weight solids of the at least one source of EGCg. Furthermore, in certain embodiments, the at least one source of EGCg contains 90-100% of EGCg by weight solids of the at least one source of EGCg.

The stability of EGCg in certain protein-containing liquid nutritional compositions is poor as it will epimerize, chemically degrade (e.g., hydrolyze, oxidize), or both epimerize and chemically degrade when the nutritional composition is subjected to heat treatment, such as the heat treatment generally associated with aseptic, retort, or hot-fill sterilization. More specifically, a certain amount of the EGCg will epimerize into its epimer GCg under certain heat treatments. Alternatively or in addition, certain protein-containing liquid nutritional compositions will lose EGCg to chemical degradation, such as hydrolysis or oxidation, during heat treatment. In particular, in certain protein-containing liquid nutritional compositions, EGCg will hydrolyze and form free gallic acid as a hydrolysis product. Thus, the respective amounts of GCg and free gallic acid present in the heat sterilized liquid nutritional compositions disclosed herein are ways to measure the amount of EGCg lost to epimerization, chemical degradation, or both epimerization and chemical degradation. Each of the GCg and the free gallic acid present in the heat sterilized liquid nutritional compositions can be measured by any known or otherwise effective technique, such as using reverse phase HPLC.

The shelf-stable, clear liquid nutritional compositions disclosed herein lose no more than 20% by weight solids of the initial amount of EGCg if subjected to heat sterilization, including in certain embodiments loss of no more than 1 to 20% by weight solids of the initial amount of EGCg. In certain of the preceding embodiments, the shelf-stable, clear liquid nutritional compositions disclosed herein lose no more than 10% by weight solids EGCg if subjected to heat sterilization. As discussed above, a way to measure the amount of loss of EGCg in a shelf-stable composition upon heat sterilization according to the embodiments disclosed herein is by measuring the amount of epimerization products, chemical degradation products, or both epimerization and chemical degradation products present in the composition following the sterilization. The shelf-stable, clear liquid nutritional compositions disclosed herein contain no more than 340 mg/L of GCg after heat sterilization, or in certain embodiments, if subjected to heat sterilization. In accordance with certain of the preceding embodiments, the shelf-stable, clear liquid nutritional composition contains no more than 3.4 to 340 mg/L of GCg, including no more than 170 mg/L of GCg after heat sterilization, or in certain embodiments, if subjected to heat sterilization. Furthermore, in certain embodiments, the shelf-stable, clear liquid nutritional compositions disclosed herein contain no more than 70 mg/L of free gallic acid after heat sterilization, or in certain embodiments, if subjected to heat sterilization. In certain of the preceding embodiments, the shelf-stable composition contains no more than 1 to 70 mg/L of free gallic acid, including no more than 25 mg/L of free gallic acid after heat sterilization, or in certain embodiments, if subjected to heat sterilization.

As previously discussed, the shelf-stable, clear liquid nutritional compositions disclosed herein include at least one source of protein in an amount sufficient to provide 25-45 g/L of total protein. In certain of the preceding embodiments, the shelf-stable, clear liquid nutritional compositions disclosed herein include at least one source of protein in an amount sufficient to provide 30-38 g/L of total protein. Suitable sources of protein include, but are not limited to, any intact, hydrolyzed, and partially hydrolyzed protein that is soluble in an aqueous composition having a pH of 2.5 to 4.6. Non-limiting examples of such suitable sources of protein include sources of whey-based proteins such as whey protein concentrates, whey protein isolates including either acidified or non-acidified whey protein isolates, whey protein hydrolysates; certain soy-based proteins such as acidified soy protein isolates and soy protein hydrolysates; certain casein-based proteins such as casein hydrolysates; certain pea-based proteins such as pea hydrolysates; and the like. The at least one source of protein can include any individual protein or combination of the various sources of protein listed above.

In certain embodiments, the at least one source of protein is selected from whey-based proteins, acidified soy protein isolates, soy protein hydrolysates, casein hydrolysates, pea hydrolysates, and combinations thereof. In accordance with certain of the preceding embodiments, the at least one source of protein is provided by whey-based protein selected from whey protein concentrates, whey protein isolates, whey protein hydrolysates, and combinations thereof. In certain other embodiments, the at least one source of protein is provided by a mixture of up to 34% of a whey-based protein by weight based on the total weight of the protein and up to 66% of a soy-based protein by weight based on the total weight of the protein.

In accordance with certain embodiments, the shelf-stable, clear liquid nutritional compositions disclosed herein contain at least one source of protein comprising β-lactoglobulin. Beta-lactoglobulin is the major whey protein found in mammalian milk, e.g., bovine and sheep milk among others. For example, β-lactoglobulin typically accounts for 50-55% by weight of the total whey protein found in bovine milk (and, overall, it accounts for 10-15% by weight of the total milk protein). Examples of whey-based proteins that provide the β-lactoglobulin suitable for complexation with EGCg in the nutritional liquids disclosed herein include the whey protein isolates and whey protein concentrates disclosed herein. In certain embodiments, suitable whey-based proteins that provide β-lactoglobulin comprise 20-95% of β-lactoglobulin by weight of the solids of the whey-based protein. In accordance with certain embodiments, the shelf-stable, clear liquid nutritional compositions disclosed herein contain at least one source of protein, such as the whey protein isolates or whey protein concentrates comprising 20-95% of β-lactoglobulin by weight of the solids of the whey-based protein.

Beta-lactoglobulin will bind with EGCg to form a β-lactoglobulin-EGCg molecular complex (also referred to herein as simply the "β-lactoglobulin-EGCg complex"). The β-lactoglobulin-EGCg complex helps prevent degradation of the EGCg in the liquid nutritional compositions during processing, e.g., sterilization, and storage by shielding the EGCg from oxidation, which in turn, helps maintain the clarity of the liquid nutritional composition. The formation of the β-lactoglobulin-EGCg complex also obscures the potent taste of the EGCg present in the nutritional compositions, which may be described as sour, astringent, and bitter taste. The β-lactoglobulin-EGCg complex also protects the EGCg from degradation during gastric digestion, as the β-lactoglobulin-EGCg complex is not readily hydrolyzed by gastric pepsin. The β-lactoglobulin-EGCg complex therefore improves the enteric delivery of the EGCg to the small intestine. Thus, the β-lactoglobulin-EGCg complex is believed to have the effect of improving the in vivo stability and bioavailability of EGCg in addition to improving the processing and storage stability of the EGCg.

In accordance with certain of the preceding embodiments, the nutritional liquid compositions disclosed herein comprise β-lactoglobulin-EGCg complexes, where the EGCg and β-lactoglobulin are present in an amount sufficient to provide a molar ratio of EGCg to β-lactoglobulin of 1:1 to 11:1 in the stabilized or unsterilized form of the composition, including a molar ratio of EGCg to β-lactoglobulin of 1:1 to 9:1, and including a molar ratio of EGCg to β-lactoglobulin of 1:1 to 7:1. Unless otherwise indicated herein, the molar ratio of EGCg to β-lactoglobulin referred to herein describes the molar ratio of these components prior to sterilization, i.e., in the stabilized or unsterilized form of the liquid nutritional compositions disclosed herein. This molar ratio range of EGCg to β-lactoglobulin provides for the maximal formation of the β-lactoglobulin-EGCg complexes in the nutritional liquid compositions while providing a clear nutritional liquid composition. Amounts outside this range lead to less clear, e.g., cloudy or opaque, liquid nutritional compositions. In accordance with certain embodiments, the shelf-stable, clear liquid nutritional compositions disclosed herein contain at least one source of protein, such as whey protein isolates or whey protein concentrates, comprising β-lactoglobulin in an amount sufficient to provide a molar ratio of EGCg to β-lactoglobulin of 1:1 to 11:1 in the composition.

In accordance with other embodiments, following sterilization, EGCg and β-lactoglobulin are present in an amount sufficient to provide a molar ratio of 0.8:1 to 11:1 in the sterilized liquid nutritional composition.

Although EGCg will bind with native β-lactoglobulin, EGCg has a greater affinity and, thus, binds more readily to the more open structure of denatured β-lactoglobulin, particularly heat denatured β-lactoglobulin, to form the β-lactoglobulin-EGCg complex. Each of native (i.e., undenatured) β-lactoglobulin, denatured β-lactoglobulin such as heat denatured β-lactoglobulin, and combinations thereof are suitable forms of β-lactoglobulin for use in certain of the embodiments of the liquid nutritional compositions disclosed herein. Thus, at least one source of protein comprising β-lactoglobulin used in accordance with certain embodiments of the liquid nutritional compositions disclosed herein contains native β-lactoglobulin, denatured β-lactoglobulin such as heat denatured β-lactoglobulin, and combinations thereof.

In accordance with certain of the embodiments disclosed herein, native β-lactoglobulin is denatured using heat. In particular, the native β-lactoglobulin is subjected to some manner of heat treatment for a period of time sufficient to denature at least a portion of the β-lactoglobulin protein. Those skilled in the art would understand that the period of time required to denature the native β-lactoglobulin depends on the type of heat treatment used, and those skilled in the art would be able to select the period of time for heat denaturing accordingly. In certain embodiments, essentially all of the β-lactoglobulin is denatured, i.e., 95-100% or 90-100% by weight, and in other embodiments less than all is denatured, i.e., 20-95% by weight.

In certain embodiments, at least a portion of the β-lactoglobulin is denatured as a result of the preparation and processing of the liquid nutritional composition. For example, the β-lactoglobulin may be denatured during the sterilization of the liquid nutritional compositions, specifically by subjecting a stabilized formulation of the liquid nutritional composition containing the β-lactoglobulin to high temperatures for a short period of time in accordance with the different sterilization techniques described in detail below. Notably, denaturing the β-lactoglobulin in the aforementioned manner, i.e., via sterilization, occurs in the presence of EGCg, because the sterilization is applied to the final formulation of the nutritional composition. Alternative to denaturing via sterilization, the β-lactoglobulin may be denatured by subjecting the β-lactoglobulin, alone or in the presence of the EGCg, to a temperature ranging from 50° C. (122° F.) to 90° C. (194° F.) for a period of time sufficient to denature at least a portion of the β-lactoglobulin, e.g., 10 to 30 minutes. In accordance with the certain of the preceding embodiments, the β-lactoglobulin may be denatured by subjecting the β-lactoglobulin, alone or in the presence of the EGCg, to a temperature ranging from 65° C. (149° F.) to 75° C. (167° F.) for a period of time sufficient to denature at least a portion of the β-lactoglobulin, e.g., 15 to 25 minutes. In certain embodiments, the denaturing of the β-lactoglobulin occurs by subjecting the β-lactoglobulin alone to denaturation or by subjecting the β-lactoglobulin and certain other ingredients of the nutritional composition to denaturation (i.e., without the EGCg present); these embodiments will further minimize loss of EGCg by heat degradation.

In accordance with certain of the preceding embodiments, when the β-lactoglobulin, or source thereof, is heat denatured in the presence of EGCg, the heat denaturing occurs at a pH level ranging from 2.5 to 4.6 because of EGCg's sensitivity to heat at higher pH's e.g., levels from 4.6 to 8. Moreover, in certain of the preceding embodiments, when the heat denaturing of the β-lactoglobulin is done independently, i.e., not in the presence of EGCg or other components, the denaturing may be performed at a pH higher than 4.6, such as a pH level from 4.6 to 8.0. However, (a) the denatured β-lactoglobulin, or source thereof, must be at a temperature ranging from 15° C. (59° F.) to 35° C. (95° F.), including from 20° C. (68° F.) to 30° C. (86° F.) (such as by allowing for cooling of the denatured β-lactoglobulin), prior to admixing with EGCg, (b) the pH of the denatured β-lactoglobulin, or source thereof must be adjusted to a level ranging from 2.5 to 4.6 prior to admixing the EGCg with the denatured protein, or (c) a combination both (a) and (c) are necessary to minimize degradation of the EGCg in the liquid nutritional composition.

In certain embodiments, the shelf-stable, clear liquid nutritional compositions disclosed herein may include at least one source of carbohydrates. In certain of the embodiments containing carbohydrates, the at least one source of carbohydrates is present in an amount sufficient to provide 30-200 g/L of carbohydrates in the shelf-stable, clear liquid nutritional composition. In certain of the preceding embodiments, the shelf-stable, clear liquid nutritional compositions disclosed herein include a source of carbohydrates in an amount sufficient to provide from 30-150 g/L of carbohydrates in the composition. Generally, any source or sources of carbohydrates may be used so long as it is suitable for use in the shelf-stable, clear liquid nutritional compositions and is otherwise compatible with any other selected ingredients or features, e.g., the EGCg, the proteins disclosed herein, pH level, etc., present in the composition. Suitable sources of carbohydrates include sources of simple carbohydrates, complex carbohydrates, or variations or combinations thereof. Non-limiting examples of sources of carbohydrates suitable for use in the liquid nutritional compositions disclosed herein include maltodextrin, hydrolyzed or modified starch or cornstarch, glucose polymers, corn syrup, corn syrup solids, rice-derived carbohydrates, sucrose, glucose, fructose, lactose, high fructose corn syrup, honey, sugar alcohols (e.g., maltitol, erythritol, sorbitol), sources of soluble fibers such as resistant starches, gum arabic, pectins, beta-glucans, and the like, and combinations thereof.

The shelf-stable, clear liquid nutritional compositions disclosed herein generally have a caloric density of about 160-1700 kcal/L. In certain embodiments, the shelf-stable, clear liquid nutritional compositions disclosed herein have a caloric density of 500-670 kcal/L. In certain embodiments, the at least one source of protein present in the shelf-stable, clear liquid nutritional composition provides substantially all of the calories in the composition. In certain other embodiments in which carbohydrates are present, the at least one source of protein and the at least one source of carbohydrates in combination provide substantially all of the calories in the composition. The amount of the at least one source of protein and, if present, the relative amount of the at least one source of carbohydrates can be adjusted to obtain the desired caloric density of the shelf-stable, clear liquid nutritional composition.

In addition, the shelf-stable, clear liquid nutritional composition disclosed herein may include at least one food-grade acid. As discussed above, the shelf-stable, clear liquid nutritional compositions disclosed herein have a pH of 2.5 to 4.6, and in certain of the preceding embodiments, a pH of 2.5 to 4, a pH of 2.5 to 3.5, or a pH of 3 to 3.5. The at least one food-grade acid may be added to the shelf-stable, clear liquid nutritional composition to adjust the pH of the overall shelf-stable, clear liquid nutritional composition to obtain a pH from 2.5 to 4.6, a pH from 2.5 to 4, a pH of 2.5 to 3.5, or a pH from 3 to 3.5. Any suitable food-grade acid that is capable of adjusting the pH of the shelf-stable, clear liquid nutritional composition to a pH ranging from 2.5 to 4.6, a pH ranging from 2.5 to 4, a pH ranging from 2.5 to 3.5, or a pH ranging from 3 to 3.5 may be used. Non-limiting examples of such suitable food-grade acids include citric acid, maleic acid, hydrochloric acid, ascorbic acid, phosphoric acid, and the like. The amount or concentration of the food-grade acid required to obtain the intended pH depends on various factors, such as the initial pH of the finalized formulation, the relative strength or weakness of the selected food-grade acid, the concentration of the selected food-grade acid, the quantity of the nutritional composition, etc. The type of acid selected may also be based on the type of flavor desired in the nutritional composition, e.g. for lemon flavored product, citric acid is more suitable, while for the apple flavored product, maleic acid is more suitable. In addition, the pH can also be adjusted by addition of clear juices, e.g. cranberry, lemon juice, lime juice, pineapple juice, and the like, including mixtures and combinations thereof, can be added to adjust the pH to desired levels. Furthermore, in the case of the over-addition of acid, a suitable food grade base, e.g., 1 N (normality) of potassium hydroxide, can be used to bring the pH of the nutritional composition to the desired level.

In certain embodiments, the shelf-stable, clear liquid nutritional compositions disclosed herein may include at least one high intensity sweetener to counter, mask, or otherwise obscure the potent taste of the EGCg present, which as mentioned above, may be described as sour, astringent, and bitter, as well as to counter, mask, or otherwise obscure the taste of any of the other polyphenols in the source of EGCg that may be present in the liquid nutritional composition. Examples of suitable high intensity sweeteners include, but are not limited to, sucralose, acesulfame potassium (also known as "acesulfame K" or "ace K"), aspartame, stevia, neotame, neohesperidine DC, alitame, monellin, thaumatin, and the like. The at least one high intensity sweetener may include any individual or combination of high intensity sweeteners listed above. The amount of the at least one high intensity sweetener in the liquid nutritional composition may vary depending upon the particular high intensity sweetener selected, other ingredients in the formulation, and other formulation or product target variables. Different high intensity sweeteners themselves have different sweetness intensities (e.g., acesulfame K is approximately 200 times sweeter than sucrose as compared to sucralose which is approximately 600 times sweeter than sucrose), and therefore may require more or less sweetener relative to other sweeteners. Furthermore, certain carbohydrates are sweeteners that may at least partially counter or at least partially mask the taste of the EGCg, and any other polyphenols that may be present, in certain embodiments of the shelf-stable, clear liquid nutritional composition disclosed herein that contain carbohydrates.

In certain embodiments, the shelf-stable, clear liquid nutritional compositions disclosed herein may also contain other ingredients, non-limiting examples of which include, preservatives; antioxidants in addition to the EGCg and other polyphenols that may be present in the at least one source of EGCg; buffers; pharmaceutical actives; additional nutrients such as amino acids; colorants; flavors; and antifoam agents.

In addition, in certain embodiments, the shelf-stable, clear liquid nutritional compositions disclosed herein may also contain vitamins or related nutrients including, but not limited to, vitamin A, vitamin E, vitamin K, thiamine, riboflavin, pyridoxine, vitamin B12, carotenoids, niacin, folic acid, pantothenic acid, biotin, vitamin C, choline, inositol, salts, and derivatives thereof, and combinations thereof.

Additionally, the shelf-stable, clear liquid nutritional compositions disclosed herein may also contain minerals, including, but not limited to, phosphorus, magnesium, iron, zinc, manganese, copper, sodium, potassium, molybdenum, chromium, selenium, chloride, and combinations thereof.

The primary constituent of the liquid phase of the shelf-stable, clear liquid nutritional compositions disclosed herein is water. The shelf-stable, clear liquid nutritional compositions contain up to about 95% water, by weight of the total liquid nutritional composition. In certain embodiments, the shelf-stable, clear liquid nutritional composition contains 80-95% water by weight of the total liquid nutritional composition. In certain and other of the preceding embodiments, the shelf-stable, clear liquid nutritional compositions disclosed herein contain 83-85% water by weight of the total liquid nutritional composition. Generally, the shelf-stable, clear liquid nutritional compositions contain an amount of water sufficient to provide the liquid nutritional composition in a serving size ranging from 100 mL to 600 mL. In certain of the preceding embodiments, the serving size includes 150 mL to 500 mL, and in certain other of the preceding embodiments, the serving size includes 175 mL to 375 mL.

The various embodiments of the shelf-stable, clear liquid nutritional compositions disclosed herein may also be substantially free of any optional ingredient or feature described herein, provided that the remaining liquid nutritional composition still contains all of the required ingredients or features as described herein. In this context, and unless otherwise specified, the term "substantially free" means that the selected shelf-stable, clear liquid nutritional compositions contain less than a functional amount of the optional ingredient, typically less than 0.5%, including less than 0.1% and also including zero, by weight of such optional ingredient.

Generally, the shelf-stable, clear liquid nutritional compositions disclosed herein contain a limited amount of fat. The limited amount of fat may be due at least in part to the desired clarity or desired pH of the composition. In certain embodiments, the shelf-stable, clear liquid nutritional compositions are substantially free of fat. As used herein "substantially free of fat" refers to shelf-stable, clear liquid nutritional compositions containing less than 0.5%, including less than 0.1% fat by weight of the total composition. "Substantially free of fat" also may refer to shelf-stable, clear liquid nutritional compositions disclosed herein that contain no fat, i.e., zero fat. In those embodiments of the shelf-stable, clear liquid nutritional compositions where some amount of fat is present, the fat may be present as a result of being inherently present in another ingredient (e.g., a source of protein) or may be present as a result of being added as one of more separate sources of fat.

As previously discussed, the shelf-stable, clear liquid nutritional compositions disclosed herein are clear. The term clear as used herein, unless otherwise specified, refers to a non-emulsified or similar other liquid having a visibly clear or translucent appearance. In certain embodiments, the term "clear" refers to shelf-stable liquid nutritional compositions, including sterilized liquid nutritional compositions and stabilized liquid nutritional compositions, that have 5 to 50 formazin nephelometric units (FNU) at 90 degree light scattering and 860 nm with a Nephla reader (Dr. Lange of Dusseldorf, Germany). In certain of the preceding embodiments, the term "clear" refers to shelf-stable liquid nutritional compositions, including sterilized liquid nutritional compositions and stabilized liquid nutritional compositions, that have less than 40 FNU at 90 degree light scattering and 860 nm with a Nephla reader.

In certain embodiments, the shelf-stable, clear liquid nutritional compositions disclosed herein are heat sterilized. Typical sterilization techniques used with the shelf-stable, clear liquid nutritional compositions disclosed herein involve some manner of heat treatment to eliminate the microorganisms capable of growth in the hermetically sealed, packaged final product, including those capable of growth at room temperature storage. Thus, in certain of the preceding embodiments, sterilized liquid nutritional products disclosed herein are hermetically sealed and packaged liquid nutritional products. Examples of suitable heat sterilization techniques used on the shelf-stable, clear liquid nutritional compositions disclosed herein include retort sterilization, aseptic sterilization, and hot-fill sterilization. The heat sterilization techniques used on the shelf-stable, clear liquid nutritional compositions disclosed herein include subjecting the compositions to temperatures ranging from 85° C. (185° F.) to 152° C. (306° F.) for a period of time sufficient to produce a sterilized liquid nutritional composition. In certain embodiments, the preparation of shelf-stable, clear liquid nutritional compositions disclosed herein includes adjusting the final pH of the composition prior to heat sterilization to a level ranging from 2.5 to 4.6, or in certain embodiments to a pH ranging from 2.5 to 4, from 2.5 to 3.5, or from 3 to 3.5. Following the adjustment of the pH, the finalized shelf-stable, clear liquid nutritional composition having a pH ranging from 2.5 to 4.6, from 2.5 to 4, from 2.5 to 3.5, or from 3 to 3.5 is a stabilized liquid nutritional composition. In the sterilized embodiments of the shelf-stable, clear liquid nutritional compositions disclosed herein, a sterilization process is applied to the stabilized liquid nutritional compositions.

In retort sterilization, the stabilized liquid nutritional composition is added to retort-stable containers, e.g., retort-stable plastic containers. The container is then hermetically sealed and subjected to a high temperature for a period of time sufficient to sterilize the product, i.e., sufficient time to kill all of the microorganisms capable of growth in the composition and in the container. Suitable retort sterilization temperatures range from 90° C. (194° F.) to 135° C. (275° F.) and these temperatures are held for a period of time sufficient to kill the microorganisms capable of growth, including those capable of growth at room temperature storage. The time required for retort sterilization generally depends on the temperature. It may take longer at lower retort temperatures to kill the microorganisms as compared to a higher retort temperature. In certain of the preceding embodiments, the retort temperatures range from 110° C. (230° F.) to 135° C. (275° F.) for a period of time sufficient to kill the microorganisms in the shelf-stable, clear liquid composition.

In one exemplary embodiment, the stabilized liquid nutritional compositions disclosed herein are sterilized via retort sterilization at a temperature of approximately 126° C. (259° F.) to 133° C. (271° F.) for at least 15 minutes.

In aseptic sterilization, the stabilized liquid nutritional composition and the container are independently sterilized before the composition is added to the container. Such a sterilization technique can generally require a shorter duration of time than retort sterilization because the separate heat treatment of the composition and container allow for more rapid heat transfer (and thus more rapid sterilizing) of each. During aseptic sterilization, the stabilized liquid nutritional composition and the container are separately subjected to temperatures ranging from 100° C. (212° F.) to 152° C. (306° F.) and these temperatures are held for a period of time sufficient to kill the microorganisms capable of growth, including those capable of growth at room temperature storage. In certain embodiments, the stabilized liquid nutritional composition and the container are separately subjected to temperatures ranging from 100° C. (212° F.) to 115° C. (239° F.). In other embodiments, the stabilized liquid nutritional composition and the container are separately subjected to temperatures ranging from 135° C. (275° F.) to 152° C. (306° F.). As mentioned above, the heat is applied for a time sufficient to kill all of the microorganisms capable of growth in the composition and the container, which may be for a shorter duration than in retort sterilization, e.g., a span lasting seconds for aseptic as compared to a span lasting minutes for retort. After the heat treatment, the composition and container are rapidly cooled, which may be done using room temperature water. The composition is then added to the container, and the container is hermetically sealed. All steps involved in the aseptic technique take place in sterile conditions.

In one exemplary embodiment, the stabilized liquid nutritional compositions disclosed herein are sterilized via aseptic sterilization at a temperature ranging from 141° C. (286° F.) to 147° C. (297° F.) for at least 10 seconds. The sterile composition and sterile container are then rapidly cooled. The sterile composition is then added to the sterile container and the container is hermetically sealed. In another exemplary embodiment, the stabilized liquid nutritional compositions disclosed herein are sterilized via aseptic sterilization at a temperature ranging from 105° C. (222° F.) to 111° C. (232° F.) for at least 5 seconds, followed by rapid cooling, adding the sterile composition to the sterile container, and hermetically sealing the container.

In hot-fill sterilization, the stabilized liquid nutritional composition is subjected to temperatures ranging from 85° C. (185° F.) to 100° C. (212° F.) for a period of time sufficient to kill all of the microorganisms capable of growth in the composition, including those capable of growth at room temperature storage. In certain of the preceding embodiments, the stabilized liquid nutritional composition is subjected to temperatures ranging from 90° C. (194° F.) to 95° C. (203° F.) for a period of time sufficient to kill the microorganisms. The time that the composition is subjected to the heat varies depending on the temperature used. After the stabilized liquid nutritional composition has been subjected to the heat for a sufficient period of time, the hot composition is added to an unsterilized container. The container is then hermetically sealed and subsequently inverted. The residual heat contained within the hot composition added to the container acts to kill the microorganisms capable of growth that are present in the unsterilized container, thereby sterilizing the final sealed and packaged product. In one exemplary embodiment, the stabilized liquid nutritional compositions disclosed herein are sterilized via hot-fill sterilization, i.e., the composition is independently heated, at a temperature of approximately 90° C. (194° F.) for at least 2 minutes. The hot composition is then added to an unsterilized container, hermetically sealed, and inverted, thereby sterilizing the container.

In accordance with another embodiment of the present disclosure, a method for preparing the sterilized, clear liquid nutritional composition is provided. The method comprises heating an unsterilized liquid nutritional composition having a pH ranging from 2.5 to 4.6 to a temperature ranging from 85° C. (185° F.) to 152° C. (306° F.) for period of time sufficient to produce a sterilized liquid nutritional composition. The sterilized liquid nutritional composition comprises water; at least one source of EGCg in an amount sufficient to provide 200-1700 mg/L of EGCg; and at least one source of protein in an amount sufficient to provide 25-45 g/L of total protein. The sterilized liquid nutritional composition contains no more than 340 mg/L of GCg. In accordance with this embodiment, the unsterilized composition having a pH level from 2.5 to 4.6 is a stabilized composition. In certain embodiments, the at least one source of protein comprises β-lactoglobulin, and wherein the unsterilized nutritional composition comprises EGCg and β-lactoglobulin in amounts sufficient to provide a molar ratio of EGCg to β-lactoglobulin of 1:1 to 11:1 in the unsterilized, i.e., stabilized composition.

In certain embodiments, the method further comprises adjusting the pH of the unsterilized liquid nutritional composition to a level ranging from 2.5 to 4.6 prior to heating. In certain embodiments, the step of heating occurs at a temperature of at least 105° C. (221° F.) for a period of time sufficient to sterilize the composition. In certain of the preceding embodiments, the step of heating occurs at a temperature of at least 126° C. (259° F.) for a period of time sufficient to sterilize the composition. Furthermore, in certain of the preceding embodiments, the pH is adjusted to a level ranging from 2.5 to 4, the pH is adjusted to a level ranging from 2.5 to 3.5, or the pH is adjusted to a level ranging from 3 to 3.5.

In certain embodiments, the method further comprises admixing at least a portion of the at least one source of EGCg with at least one source of protein containing β-lactoglobulin. The admixing of the at least one source of EGCg and the at least one source of protein containing β-lactoglobulin allows for maximal formation of the EGCg-β-lactoglobulin complex. The step of admixing occurs at a pH level ranging from 2.5 to 4.6 and occurs prior to heating the unsterilized liquid nutritional composition. In certain of the preceding embodiments, at least a portion of the β-lactoglobulin is already denatured upon admixing. In accordance with certain of the preceding embodiments, the method further comprises denaturing at least a portion of the β-lactoglobulin prior to admixing. In accordance with the preceding embodiment, the step of denaturing at least a portion of the β-lactoglobulin includes heating the at least one source of protein containing β-lactoglobulin to a temperature ranging from 50° C. (122° F.) to 90° C. (194° F.) for a period of time sufficient to denature at least a portion of the β-lactoglobulin. Furthermore, in accordance with the preceding embodiment, the at least one source of protein containing β-lactoglobulin is at a temperature ranging from 15° C. (59° F.) to 35° C. (95° F.) prior to admixing (i.e., mixing of the β-lactoglobulin with the EGCg).

In another embodiment, a method for preparing a sterilized, clear liquid nutritional composition is provided. The method comprises admixing at least one source of epigallocatechin gallate (EGCg) and at least one source of whey-based protein containing β-lactoglobulin to form an admixture, where the admixture comprises EGCg and β-lactoglobulin in amounts sufficient to provide a molar ratio of EGCg to β-lactoglobulin of 1:1 to 11:1 in the admixture. The admixing occurs at a pH of 2.5 to 4.6. The method also includes a step directed to forming an unsterilized liquid nutritional composition by combining the admixture with at least one of the following ingredients: water; an additional source of EGCg; and an additional source of protein selected from the group consisting of whey-based proteins, acidified soy protein isolates, soy protein hydrolysates, casein hydrolysates, pea hydrolysates, and combinations thereof. In addition, the method includes the steps of adjusting the pH of the unsterilized nutritional composition to obtain a pH ranging from 2.5 to 4.6, if necessary, and heating the unsterilized liquid nutritional composition to a temperature ranging from 85° C. (185° F.) to 152° C. (306° F.) for a period of time sufficient to produce a sterilized liquid nutritional composition. The sterilized nutritional composition produced according to this method comprises water, 200-1700 mg/L of total EGCg, 25-45 g/L of total protein, and no more than 340 mg/L of gallocatechin gallate (GCg).

In accordance with certain of the preceding embodiments, at least a portion of the at least one source of whey-based protein containing β-lactoglobulin in the admixture includes denatured β-lactoglobulin. In certain of the preceding embodiments, the method further comprises denaturing at least a portion of the at least one source of whey-based protein containing β-lactoglobulin by heating the at least one source of whey-based protein containing β-lactoglobulin to a temperature ranging from 50° C. (122° F.) to 90° C. (194° F.) for a period of time sufficient to denature at least a portion of the β-lactoglobulin. In accordance with certain of the preceding embodiments, the at least one source of protein containing β-lactoglobulin is at a temperature ranging from 15° C. (59° F.) to 35° C. (95° F.) prior to admixing.

In accordance with certain of the preceding embodiments, the shelf-stable, clear liquid nutritional compositions disclosed herein include ready-to-drink liquid nutritional products. As used herein "ready-to-drink" refers to a product which may be consumed without further preparation, i.e., it does not need to be mixed, cooked, etc. Both the stabilized and sterilized liquid nutritional products disclosed herein may be in the form of ready-to-drink products. The ready-to-drink liquid nutritional products comprising the sterilized liquid nutritional compositions disclosed herein have a long shelf-life and can be stored at ambient or room temperature, i.e., generally 18° C. (64° F.) to 25° C. (77° F.), for up to 12 months following sterilization. The ready-to-drink liquid nutritional products comprising the stabilized liquid nutritional compositions disclosed herein have a relatively shorter shelf-life than the sterilized embodiments and may require refrigeration depending on the length that the product is stored.

EXAMPLES

The following examples illustrate specific and exemplary embodiments and/or features of the shelf-stable, clear liquid nutritional compositions disclosed herein. The examples are provided solely for the purposes of illustration and should not be construed as limitations of the present disclosure. Numerous variations over these specific examples are possible without departing from the spirit and scope of the presently disclosed liquid nutritional compositions. All amounts indicated within the tables below are weight percentages based upon the total weight of the composition, unless indicated otherwise.

Examples 1-4

Four shelf-stable, clear liquid nutritional compositions were prepared according to the formulations shown in Table 1. All ingredient amounts listed in Table 1 are listed as kilogram per 1000 kg batch of product, unless otherwise indicated. The amount of the green tea extract varies in Examples 1-4. The amount added to the compositions of Examples 1 and 3 corresponds to a target of about 1278 mg/L of green tea extract in the composition. Approximately 50% by weight of the green tea extract used is EGCg. Thus, the compositions of Examples 1 and 3 contain a target amount of about 639 mg/L EGCg. The amount added to the compositions of Examples 2 and 4 corresponds to about 1765 mg/L of green tea extract in the composition. Again, because the green tea extract contains approximately 50% by weight of EGCg, this corresponds to a target amount of about 883 mg/L EGCg in the compositions of Examples 2 and 4. The compositions of Examples 1-4 have a target level of about 30.5 g/L of protein.

TABLE 1

| INGREDIENTS | Example 1 | Example 2 | Example 3 | Example 4 |
| --- | --- | --- | --- | --- |
| Water | Quantity Sufficient | Quantity Sufficient | Quantity Sufficient | Quantity Sufficient |
| Sucrose | 50.7 | 50.7 | 36.25 | 36.75 |
| Corn syrup solids | 61.3 | 61.3 | 51.63 | 51.63 |
| Acidified Soy Protein Isolate | — | — | 21.71 | 21.71 |
| Acidified Whey Protein Isolate | 35.7 | 35.7 | 10.89 | 10.89 |
| Wheat dextrin or resistant starch dietary fiber | — | — | 7.51 | 7.51 |
| Barley-beta-glucan concentrate (70%) | — | — | 3.71 | 3.71 |
| Citric Acid | 2.00 | 2.00 | 2.00 | 2.00 |

TABLE 1-continued

| INGREDIENTS | Example 1 | Example 2 | Example 3 | Example 4 |
|---|---|---|---|---|
| Flavoring | 2.00 | 2.00 | 2.00 | 2.00 |
| EGCg-containing Green Tea Extract[1] | 1.212 | 1.675 | 1.212 | 1.675 |
| Ascorbic Acid | 0.535 | 0.535 | 0.535 | 0.535 |
| L-Carnitine | — | — | 0.321 | 0.321 |
| Liquid Sucralose (25%) | 0.275 | 0.300 | 0.275 | 0.300 |
| UTM/TM Premix[2] | 0.230 | 0.230 | 0.230 | 0.230 |
| Vitamin Premix[3] | 0.219 | 0.219 | 0.219 | 0.219 |
| Acesulfame Potassium | 0.110 | 0.110 | 0.110 | 0.110 |
| Antifoam processing aid (non-silicone) | 0.060 | 0.060 | 0.060 | 0.060 |
| Coloring | 0.0589 | 0.0589 | 0.0589 | 0.0589 |
| Folic Acid | 0.0013 | 0.0013 | 0.0013 | 0.0013 |
| Potassium Iodide | 0.000204 | 0.000204 | 0.000204 | 0.000204 |

[1]SUNPHENON ® 90D (available from Taiyo International, Inc. of Minneapolis, Minnesota) is a green tea extract that contains approximately 50% by weight EGCg.
[2]UTM/TM premix is a mineral premix that includes ultra trace and trace minerals.
[3]Vitamin premix includes one or more of the following: dl-Alpha-Tocopheryl Acetate, Vitamin A Palmitate, Phylloquinone, Vitamin D3, Niacinamide, d-Calcium Pantothenate, Thiamine Chloride Hydrochloride, Pyridoxine Hydrochloride, Riboflavin, Folic Acid, Biotin, Cyanocobalamin, etc.

The compositions of Examples 1 and 2 were prepared in the same manner. In particular, all except about 1.36 kg of the total water was added to a kettle. The protein was then added to the water in the kettle, and this mixture was agitated for 10 minutes or until all of the protein dissolved into solution. The remaining ingredients, except the green tea extract and citric acid, were then added to form a mixture. After the addition of the remaining ingredients and before the green tea extract was added, the pH of the mixture was adjusted to a target pH of 3.2 by adding the citric acid. A solution of the green tea extract was prepared in a separate kettle, with the amount listed in Table 1 for each respective Example being added to 0.908 kg of water. Then, the prepared green tea extract solution was added to the mixture of each batch. The pH of the resulting compositions was then measured to confirm that each was within the range of 3-3.4.

The compositions of Examples 3 and 4 were prepared in the same manner as those of Examples 1 and 2 except that the initial quantity of water added to the kettle was first divided into two parts. One part of the water was heated to about 66° C. (150° F.) prior to adding the beta-glucan, the wheat dextrin, and the acidified soy protein isolate to it, and this mixture was agitated until a homogeneous solution was obtained. The hot solution was then mixed with the second part water, i.e., the cold water, after which the process described above for the compositions of Examples 1 and 2 were followed.

As shown in Table 1, the compositions of Examples 1-4 all contain a whey-based protein, i.e., an acidified whey protein isolate. The acidified whey protein isolate contains approximately 90% of whey protein solids by the total weight of the isolate. In this isolate, approximately 50% of the whey protein solids is β-lactoglobulin. Given the approximate amounts of EGCg for the compositions of Examples 1-4 as discussed above, the molar ratio of EGCg to β-lactoglobulin was determined and shown in Table 2 below.

TABLE 2

| Ingredient | Example 1 | Example 2 | Example 3 | Example 4 |
|---|---|---|---|---|
| Acidified Whey Protein Isolate (kg/1000 kg) | 35.7 | 35.7 | 10.89 | 10.89 |

TABLE 2-continued

| Ingredient | Example 1 | Example 2 | Example 3 | Example 4 |
|---|---|---|---|---|
| β-lactoglobulin (kg/1000 kg) | 16.1 | 16.1 | 4.90 | 4.90 |
| β-lactoglobulin (molar) | 880 mmoles per 1000 kg | 880 mmoles per 1000 kg | 270 mmoles per 1000 kg | 270 mmoles per 1000 kg |
| EGCg-containing Green Tea Extract (kg/1000 kg) | 1.212 | 1.675 | 1.212 | 1.675 |
| EGCg (kg/1000 kg) | 0.606 | 0.838 | 0.606 | 0.838 |
| EGCg (molar) | 1320 mmoles per 1000 kg | 1830 mmoles per 1000 kg | 1320 mmoles per 1000 kg | 1830 mmoles per 1000 kg |
| EGCg to β-lactoglobulin (molar ratio) | 1.50 | 2.08 | 4.89 | 6.78 |

Separate samples of each composition of Examples 1-4 were then subjected to aseptic sterilization, i.e., the container and composition sterilized separately, or retort sterilization, i.e., the composition is sealed in the container prior to retort sterilization. The aseptic sterilization was carried out at about 106-111° C. (about 222-232° F.) for 5 seconds. The retort sterilization was carried out at about 127-132° C. (260-270° F.) for 15 minutes. The amount of EGCg present in the compositions of Examples 1-4 was measured by reverse phase HPLC using a YMC ODS-AQ, S-5, 120 A, 4.6×250 mm column and using an acetonitrile gradient. The parameters of the HPLC system used in these Examples are listed below. The reference materials used to calibrate the HPLC were the same solutions of the green tea extract used in the Examples above, which had known concentrations of EGCg. The HPLC is a Model 1200 System (available from Agilent Technologies of Wilmington, Del.). For each respective composition (i.e., each of Examples 1-4), the amount of EGCg was measured in an unsterilized sample, a sample subjected to aseptic sterilization, and a sample subjected to retort sterilization. The results of these measurements are reported in Table 3 below, including the target amount of EGCg added to each composition.

HPLC System Parameters:
  Column: YMC ODS-AQ S-5 120 A 4.6×250 mm, YMC Part Number AQ12S052546WT,
  Mobile Phase A: 950 mL 0.05 M KH2PO4, pH 2.9; 50 mL acetonitrile, Mobile Phase B: 200 mL Milli-Q Plus water, 800 mL acetonitrile,
Flow Rate: 0.5 mL/minute,
Temperature: 40° C.,
Detection: UV at 280 nm,
Injection: 5 microliters.
Run Time: 45 minutes,
Elution Program: 0% B from 0-5 minutes, 0-50% B from 5-30 minutes, 100% B from 30-35 minutes, 0% B from 35-45 minutes.

TABLE 3

|  | Example 1 | Example 2 | Example 3 | Example 4 |
|---|---|---|---|---|
| Target EGCg Amount (mg/L) | 639 | 883 | 639 | 883 |
| EGCg in Unsterilized Sample (mg/L) | 636 | 872 | 637 | 849 |
| % of Target | 99.5% | 98.9% | 99.7% | 96.2% |
| EGCg in Aseptic Sample (mg/L) | 626 | 866 | 597 | 822 |
| % of Target | 97.9% | 98.1% | 93.4% | 93.1% |
| EGCg in Retort Sample (mg/L) | 566 | 778 | 544 | 739 |
| % of Target | 88.6% | 88.1% | 85.2% | 83.7% |

As shown in Table 3, generally more than 80% of the target amount of EGCg initially present in the composition of Examples 1-4 before sterilization remained in the composition following heat sterilization by either method. Accordingly, generally no more than 20% of the initial EGCg present in the compositions of Examples 1-4 was lost during the heat treatment of the aseptic and retort sterilizations applied to the respective samples. In particular, greater than 93% of the target EGCg was recovered in Examples 1-4 following aseptic sterilization. For the aseptically sterilized samples, Example 4 had the lowest recovery of EGCg at 93.1% of the target amount of EGCg. For retort sterilization, greater than 83% of the EGCg was generally recovered in the composition following sterilization. For the retort sterilized samples, Example 4 had the lowest recovery of EGCg at 83.7% of the target amount of EGCg following retort sterilization. Notably, the compositions of Examples 1 and 2 generally have higher recoveries than the compositions of Examples 3 and 4 (for both aseptic and retort sterilization). Without intending to be limited by any theory, it is believed that the difference in EGCg recovery between Examples 1-2 and 3-4 is attributable to the types of proteins contained in the composition. The compositions of Examples 3 and 4 contain a mixture of acidified soy protein isolate and acidified whey protein isolate, while the composition of Examples 1 and 2 contain only an acidified whey protein isolate. It is believed that the presence of relatively more β-lactoglobulin for the amount of EGCg present in the compositions of Examples 1 and 2, as a result of the proteins that were used and as shown by the molar ratios of EGCg to β-lactoglobulin in Table 2, provided for more complexation of the EGCG with the β-lactoglobulin, thereby protecting the EGCg from degradation due to oxidation.

Comparative Examples 5-6

Two liquid nutritional compositions were prepared according to the formulations shown in Table 4. All ingredient amounts listed in Table 4 are listed as kilogram per 1000 kg batch of product, unless otherwise indicated. The amounts of the green tea extract differ in Comparative Examples 5 and 6. The amount added to the composition of Comparative Example 5 corresponds to a target of about 1475 mg/L of green tea extract in the composition. The green tea extract contains approximately 50% EGCg, and therefore, the target amount of EGCg added in the composition of Comparative Example 5 is about 738 mg/L. The amount added to the composition of Comparative Example 6 corresponds to about 2110 mg/L of green tea extract in the composition. Again, because the green tea extract contains approximately 50% of EGCg, this corresponds to a target EGCg amount of about 1055 mg/L in Comparative Example 6. Comparative Examples 5 and 6 contain a target level of 38 g/L protein.

TABLE 4

| INGREDIENTS | Comparative Example 5 | Comparative Example 6 |
|---|---|---|
| Water | Quantity Sufficient | Quantity Sufficient |
| EGCg-containing Green Tea Extract[1] | 1.390 | 1.984 |
| Sucrose | 89.1 | 89.1 |
| Maltodextrin | 69.1 | 69.1 |
| Milk Protein Concentrate | 38.6 | 38.6 |
| Soy Oil | 13.3 | 13.3 |
| Canola Oil | 5.3 | 5.3 |
| Soy Protein Concentrate | 4.7 | 4.7 |
| Corn Oil | 4.1 | 4.1 |
| Potassium Citrate | 2.7 | 2.7 |
| Flavoring | 2.0 | 2.0 |
| Magnesium Phosphate Dibasic | 1.9 | 1.9 |
| Sodium Citrate | 1.6 | 1.6 |
| Soy Lecithin | 1.4 | 1.4 |
| Tricalcium Phosphate | 1.3 | 1.3 |
| Magnesium Chloride | 1.2 | 1.2 |
| Sodium Chloride | 0.718 | 0.718 |
| Choline Chloride | 0.480 | 0.480 |
| Ascorbic Acid | 0.469 | 0.469 |
| Carrageenan | 0.450 | 0.450 |
| UTM/TM Premix[2] | 0.364 | 0.364 |
| Potassium Hydroxide (Processing aid) | 0.323 | 0.323 |
| Potassium Chloride | 0.308 | 0.308 |
| Vitamin Premix[3] | 0.1465 | 0.1465 |
| Potassium Iodide | 0.000207 | 0.000207 |

[1]SUNPHENON ® 90D.
[2]Same UTM/TM premix as disclosed in Table 1 (mineral premix that includes ultra trace and trace minerals).
[3]Same Vitamin premix as disclosed in Table 1 (includes one or more of the following: dl-Alpha-Tocopheryl Acetate, Vitamin A Palmitate, Phylloquinone, Vitamin D3, Niacinamide, d-Calcium Pantothenate, Thiamine Chloride Hydrochloride, Pyridoxine Hydrochloride, Riboflavin, Folic Acid, Biotin, Cyanocobalamin, etc.).

Both of these compositions were prepared in the following manner. At least three separate slurries for each composition were prepared. These slurries include: a protein-in-fat (PIF) slurry, a carbohydrate-mineral (CHO-MIN) slurry, and a protein-in-water (PIW) slurry. The PIF slurry was formed by heating and mixing any oils and then adding an emulsifier (e.g., lecithin), fat-soluble vitamins, and a portion of the total protein with continued heat and agitation. The CHO-MIN slurry was formed by adding to water with heat and agitation, minerals (e.g., potassium citrate, sodium citrate, etc.), trace and ultra trace minerals (in the premix), and any thickening-type or suspending agents (e.g., carrageenan). The resulting CHO-MIN slurry was held for 10 minutes with continued heat and agitation, and then additional minerals (e.g., potassium chloride, potassium iodide, etc.) and the carbohydrates (e.g., sucrose, maltodextrin, etc.) were added. The PIW slurry was formed by mixing the remaining protein into water.

The three slurries were blended together with heat and agitation, and the pH was adjusted to the desired range from 6.6 to 7, after which the composition was subjected to high-temperature short-time ("HTST") processing. The composition was heat treated, emulsified, and homogenized and allowed to cool during HTST. Water soluble vitamins and ascorbic acid were added, the pH was again adjusted (if necessary), flavors were added and any additional water was added to adjust the solids content to the desired range. A green tea solution (1%) was made by adding the green tea extract to room temperature water. The green tea solution was then added to the composition. The composition was agitated for about 5 minutes to ensure homogeneous distribution of green tea solution in the composition. The final pH of these compositions before sterilization was from 6.7-7.0.

Separate samples of each composition of Comparative Examples 5 and 6 were then subjected to aseptic and retort sterilization. The aseptic sterilization was done at about 141-147° C. (about 286-296° F.) for 10 seconds, while retort sterilization was done at about 129° C. (about 265° F.) for 15 minutes. The respective amounts of EGCg present in the compositions of Comparative Examples 5 and 6 were measured by reverse phase HPLC using the same equipment and parameters as described above for Examples 1-4. For each respective composition (i.e., each of Comparative Examples 5 and 6), the amount of EGCg was measured in an unsterilized sample, a sample subjected to aseptic sterilization, and a sample subjected to retort sterilization. In the sterilized samples, the amount of GCg was also measured by reverse phase HPLC using the same equipment and parameters as described above [because EGCg and GCg are isomers, they are assumed to exhibit the same detector response, so that the same response factor (calibration curve) was used for both EGCg and for GCg]. The results of these measurements are reported in Table 5 below as the percent recovery of the targeted EGCg amounts added to the compositions.

As shown in Table 5, the comparative liquid nutritional compositions of Examples 5 and 6 which have neutral pH of about 6.7-7.0 at the time of sterilization, generally recover significantly less EGCg than the example embodiments of the shelf-stable, clear liquid nutritional compositions disclosed in Examples 1-4 which have a pH ranging from 3-3.4. Less than 46% of the target EGCg, i.e., 44.8% (Example 5) and 45.8% (Example 6), was recovered in these compositions following aseptic sterilization as compared to greater than 93% of the target EGCg recovered in Examples 1-4 following aseptic sterilization. Similarly, significantly less EGCg was recovered following retort sterilization in the compositions of Comparative Examples 5 and 6 as compared to the samples subjected to retort sterilization in Examples 1-4. In particular, less than 340%, i.e., 32.2% (Example 5) and 33.7% (Example 6), of the target EGCg was recovered in the compositions of Comparative Examples 5 and 6 as compared to the greater than 83% of the EGCg was recovered in the compositions of Examples 1-4 following retort sterilization. As shown in Table 5, much of the EGCg was lost to epimerization to GCg. This is evidenced by the greater than a 90% combined recovery of EGCg and GCg following aseptic sterilization in Comparative Examples 5 and 6 and the greater than a 75% combined recovery of EGCg and GCg following retort sterilization.

Examples 7-13

Seven shelf-stable, clear liquid nutritional compositions were prepared according to the formulations shown in Table 6. All ingredient amounts listed in Table 6 are listed as kilogram per 1000 kg batch of product, unless otherwise indicated. The amount of the green tea extract varies for the compositions of Examples 7-10 which contain one level of protein, and the amount of the green tea extract varies in the compositions of Examples 11-13 at another level of protein. In particular, the compositions in Examples 7-10 have a target level of about 30.5 mg/L of protein and various target amounts of EGCg ranging from 0 (Example 7) to about 1690 mg/L (Example 10). Examples 11-13 have a target level of about 40.6 mg/L of protein and various target amounts of EGCg ranging from 0 (Example 7) to about 1691 mg/L (Example 13). As in Examples 1-4 and Comparative Examples 5-6, green tea extract is the source of EGCg in the compositions of Examples 8-10 and 12-13, and the green tea extract contains approximately 50% EGCg by weight.

TABLE 5

|  | Comparative Example 5 | Comparative Example 6 |
|---|---|---|
| Target EGCg Amount (mg/L) Unsterilized | 1475 | 2110 |
| EGCg as % of Target | 101.3% | 102.6% |
| EGCg + GCg as % of Target | N/A | N/A |
| Aseptic |  |  |
| EGCg as % of Target | 44.8% | 45.8% |
| EGCg + GCg as % of Target | 93.4% | 94.5% |
| Retort |  |  |
| EGCg as % of Target | 32.2% | 33.7% |
| EGCg + GCg as % of Target | 75.8% | 80.2% |

TABLE 6

| INGREDIENTS | Example 7 | Example 8 | Example 9 | Example 10 | Example 11 | Example 12 | Example 13 |
|---|---|---|---|---|---|---|---|
| Water | Q.S. | Q.S. | Q.S. | Q.S. | Q.S. | Q.S. | Q.S. |
| Sucrose | 50.7 | 50.7 | 50.7 | 50.7 | 50.7 | 50.7 | 50.7 |
| Corn syrup solids | 61.3 | 61.3 | 61.3 | 61.3 | 61.3 | 61.3 | 61.3 |
| Acidified Whey Protein Isolate | 12.5 | 12.5 | 12.5 | 12.5 | 16.7 | 16.7 | 16.7 |
| Citric Acid | 2.00 | 2.00 | 2.00 | 2.00 | 2.00 | 2.00 | 2.00 |
| Flavoring | 2.50 | 2.50 | 2.50 | 2.50 | 2.50 | 2.50 | 2.50 |

TABLE 6-continued

| INGREDIENTS | Example 7 | Example 8 | Example 9 | Example 10 | Example 11 | Example 12 | Example 13 |
|---|---|---|---|---|---|---|---|
| EGCg-containing Green Tea Extract[1] | 0 | 1.215 | 2.432 | 3.221 | 0 | 2.427 | 3.204 |
| Ascorbic Acid | 0.535 | 0.535 | 0.535 | 0.535 | 0.535 | 0.535 | 0.535 |
| Liquid Sucralose (25%) | 0.275 | 0.275 | 0.275 | 0.275 | 0.275 | 0.275 | 0.275 |
| UTM/TM Premix[2] | 0.230 | 0.230 | 0.230 | 0.230 | 0.230 | 0.230 | 0.230 |
| Vitamin Premix[3] | 0.218 | 0.218 | 0.218 | 0.218 | 0.218 | 0.218 | 0.218 |
| Acesulfame Potassium | 0.110 | 0.110 | 0.110 | 0.110 | 0.110 | 0.110 | 0.110 |
| antifoam processing aid (non-silicone) | 0.060 | 0.060 | 0.060 | 0.060 | 0.060 | 0.060 | 0.060 |
| Coloring | 0.708 | 0.708 | 0.708 | 0.708 | 0.708 | 0.708 | 0.708 |
| Folic Acid | 0.0013 | 0.0013 | 0.0013 | 0.0013 | 0.0013 | 0.0013 | 0.0013 |
| Potassium Iodide | 0.000204 | 0.000204 | 0.000204 | 0.000204 | 0.000204 | 0.000204 | 0.000204 |

[1]SUNPHENON ® 90D.
[2]Same UTM/TM premix as disclosed in Table 1 (mineral premix that includes ultra trace and trace minerals).
[3]Same Vitamin premix as disclosed in Table 1 (includes one or more of the following: dl-Alpha-Tocopheryl Acetate, Vitamin A Palmitate, Phylloquinone, Vitamin D3, Niacinamide, d-Calcium Pantothenate, Thiamine Chloride Hydrochloride, Pyridoxine Hydrochloride, Riboflavin, Folic Acid, Biotin, Cyanocobalamin, etc.).

The compositions of Examples 7-13 were prepared in the same manner as those described in Examples 1 and 2, except that the solution of green tea extract was prepared using 2.27 kg of water. The pH of the resulting mixtures was then measured to confirm the respective solutions were within the range of 3-3.4.

Separate samples of each composition of Examples 7-13 were then subjected to aseptic sterilization under the same aseptic conditions described above for Examples 1-4. The amount of EGCg present in the compositions of Examples 7-13 was measured by reverse phase HPLC using the same equipment and parameters as described above for Examples 1-4. For each respective composition (i.e., each of Examples 7-13), the amount of EGCg was measured in an unsterilized sample and a sample subjected to the sterilization. The results of these measurements are reported in Table 7 below as the percent of the targeted EGCg amounts added to the compositions.

TABLE 7

| | Example 7 | Example 8 | Example 9 | Example 10 | Example 11 | Example 12 | Example 13 |
|---|---|---|---|---|---|---|---|
| Target EGCg Amount (kg/1000 kg) | 0 | 0.634 | 1.268 | 1.691 | 0 | 1.268 | 1.691 |
| Target amount of β-lactoglobulin (kg/1000 kg) | 5.625 | 5.625 | 5.625 | 5.625 | 7.515 | 7.515 | 7.515 |
| Unsterilized | | | | | | | |
| EGCg (kg/1000 kg) | 0 | 0.565 | 1.155 | 1.530 | 0 | 1.165 | 1.570 |
| EGCg: β-LG, molar ratio | 0 | 4.01 | 8.21 | 10.9 | 0 | 6.18 | 8.33 |
| EGCg as % of Target | N/A | 93% | 95% | 95% | N/A | 96% | 98% |
| Sterilized | | | | | | | |
| EGCg (kg/1000 kg) | 0 | 0.565 | 1.125 | 1.480 | 0 | 1.135 | 1.510 |
| EGCg as % of Unsterilized | N/A | 100% | 97% | 97% | N/A | 97% | 96% |

As shown in Table 7, generally more than 95% of the target amount of EGCg initially present in the composition of Examples 8-13 before sterilization remained in the composition following sterilization. Accordingly, generally no more than 5% of the initial EGCg present in the compositions of Examples 8-13 was lost during the heat treatment of the sterilization applied to each of the respective samples. In particular, 100% of the target EGCg was recovered in Example 8 following sterilization. Example 13 had the lowest recovery of EGCg at 96% of the amount of EGCg prior to sterilization.

Unless otherwise indicated herein, all sub-embodiments and optional embodiments are respective sub-embodiments and optional embodiments to all embodiments described herein. While the present application has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art. Therefore, the application, in its broader aspects, is not limited to the specific details, the representative apparatus, and illustrative examples shown and described. Accordingly, departures may be made from such details without departing from the spirit or scope of the applicant's general inventive concept.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See Bryan A. Garner, *A Dictionary of Modern Legal Usage* 624 (2d. Ed. 1995). Also, to the extent that the terms "in" or "into" are used in the specification or the claims, it is intended to additionally mean "on" or "onto." Furthermore, to the extent the term "connect" is used in the specification or claims, it is intended to mean not only "directly connected to," but also "indirectly connected to" such as connected through another component or components.

What is claimed is:

1. A method for preparing a sterilized, clear liquid nutritional composition, the method comprising:
    heating an unsterilized liquid nutritional composition having a pH ranging from 2.5 to 4.6 to a temperature ranging from 85° C. (185° F.) to 152° C. (306° F.) for a period of time sufficient to produce a sterilized liquid nutritional composition, thereby producing a sterilized liquid nutritional composition comprising:
        water;
        at least one source of epigallocatechin gallate (EGCg) in an amount sufficient to provide 200-1700 g/L of EGCg; and
        one or more sources of protein in an amount sufficient to provide 25-45 g/L of total protein, wherein the one or more sources of protein comprise whey protein concentrate, whey protein isolates; and/or whey protein hydrosylates;
    wherein:
        the whey protein concentrate, whey protein isolates, and/or whey protein hydrosylates comprise β-lactoglobulin;
        the sterilized liquid nutritional composition contains no more than 340 mg/L of gallocatechin gallate (GCg), and
        the sterilized liquid nutritional composition is clear.

2. The method of claim 1 further comprising adjusting the pH of the unsterilized liquid nutritional composition to a level ranging from 2.5 to 4.6 prior to the heating.

3. The method of claim 1, wherein the whey protein concentrate, whey protein isolates, and/or whey protein hydrosylates comprise β-lactoglobulin in an amount sufficient to provide a molar ratio of EGCg to β-lactoglobulin of 1:1 to 11:1 prior to sterilization.

4. The method of claim 1, wherein the at least one source of EGCg is a green tea-based source of EGCg.

5. The method of claim 1, wherein the at least one source of EGCg comprises 45% to 100% by weight solids of EGCg based on the weight of the at least one source of EGCg.

6. The method of claim 1, wherein the sterilized liquid nutritional composition further comprises acidified soy protein isolates, soy protein hydrolysates, casein hydrolysates, or pea hydrolysates.

7. The method of claim 1, wherein the one or more sources of protein comprise whey-based protein containing 20% to 95% of β-lactoglobulin by weight of the solids of the whey-based protein.

8. The method of claim 1, wherein no more than 170 mg/L of GCg is present in the sterilized liquid nutritional composition.

9. The method of claim 1, wherein the heating occurs at a temperature of at least 105° C. (221° F.) for a period of time sufficient to sterilize the composition.

10. The method claim 1, wherein the heating occurs at a temperature of at least 126° C. (259° F.) for a period of time sufficient to sterilize the composition.

11. The method of claim 1, further comprising adjusting the pH level of the sterilized liquid nutritional composition to a range of 2.5 to 3.5.

12. The method of claim 1, further comprising admixing at least a portion of the at least one source of EGCg with the one or more sources of protein, wherein the step of admixing occurs at a pH ranging from 2.5 to 4.6 and occurs prior to the heating of the unsterilized liquid nutritional composition.

13. The method of claim 12, wherein at least a portion of the β-lactoglobulin is denatured upon admixing.

14. The method of claim 12, further comprising denaturing at least a portion of the β-lactoglobulin prior to admixing.

15. The method of claim 14, wherein the step of denaturing the at least a portion of the β-lactoglobulin includes heating the one or more sources of protein containing β-lactoglobulin to a temperature ranging from 50° C. (122° F.) to 90° C. (194° F.) for a period of time sufficient to denature the at least a portion of the β-lactoglobulin.

16. The method of claim 12, wherein the one or more sources of protein containing β-lactoglobulin is at a temperature ranging from 15° C. (59° F.) to 35° C. (95° F.) prior to admixing with the at least one source of EGCg.

17. The method of claim 1, wherein the sterilized composition has a pH at a level ranging from 2.5 to 4.

18. The method of claim 1, wherein the sterilized composition further comprises at least one source of carbohydrate, and the at least one source of carbohydrate is present in an amount sufficient to provide 30-200 g/L of carbohydrate.

19. The method of claim 1, further comprising admixing at least a portion of the at least one source of EGCg with the one or more sources of protein prior to the heating step and denaturing at least a portion of the β-lactoglobulin prior to the admixing.

20. The method of claim 1, further comprising:
    admixing, prior to the step of heating, the at least one source of epigallocatechin gallate (EGCg) and the one or more sources of protein comprising β-lactoglobulin to form an admixture; and
    forming an unsterilized liquid nutritional composition by combining the admixture with at least one of the following ingredients:
        water;
        an additional source of EGCg; and
        an additional source of protein selected from the group consisting of acidified soy protein isolates, soy protein hydrolysates, casein hydrolysates, pea hydrolysates, and a combination thereof.

21. A method for preparing a sterilized, clear liquid nutritional composition, the method comprising:
    admixing at least one source of epigallocatechin gallate (EGCg) and at least one source of whey-based protein containing β-lactoglobulin to form an admixture, wherein the admixture comprises EGCg and β-lactoglobulin in amounts sufficient to provide a molar ratio of EGCg to β-lactoglobulin of 1:1 to 11:1 in the admixture, and wherein the admixing occurs at a pH of 2.5 to 4.6;

forming an unsterilized liquid nutritional composition by combining the admixture with at least one of the following ingredients:
water;
an additional source of EGCg; and
an additional source of protein selected from the group consisting of whey-based proteins, acidified soy protein isolates, soy protein hydrolysates, casein hydrolysates, pea hydrolysates, and combinations thereof;

adjusting the pH of the unsterilized nutritional composition to obtain a pH ranging from 2.5 to 4.6 if necessary; and heating the unsterilized liquid nutritional composition to a temperature ranging from 85° C. (185° F.) to 152° C. (306° F.) for a period of time sufficient to produce a sterilized liquid nutritional composition comprising:
water,
200-1700 mg/L of total EGCg,
25-45 g/L of total protein, and
no more than 340 mg/L of gallocatechin gallate (GCg), wherein the sterilized liquid nutritional composition is clear.

22. The method of claim 21, wherein at least a portion of the at least one source of whey-based protein containing β-lactoglobulin in the admixture includes denatured β-lactoglobulin.

23. The method of claim 21 further comprising denaturing at least a portion of the at least one source of whey-based protein containing β-lactoglobulin by heating the at least one source of whey-based protein containing β-lactoglobulin to a temperature ranging from 50° C. (122° F.) to 90° C. (194° F.) prior to the admixing for a period of time sufficient to denature at least a portion of the β-lactoglobulin.

24. The method of claim 23, wherein the at least one source of protein containing β-lactoglobulin is at a temperature ranging from 15° C. (59° F.) to 35° C. (95° F.) prior to admixing.

25. The method of claim 21, wherein the sterilized liquid nutritional composition further comprises at least one source of carbohydrate in an amount sufficient to provide 30-200 g/L of carbohydrate in the composition.

26. A sterilized, clear liquid nutritional composition comprising:
water;
at least one source of epigallocatechin gallate (EGCg) in an amount sufficient to provide 675-1525 mg/L of the EGCg; and
one or more sources of protein in an amount sufficient to provide 25-45 g/L of total protein, wherein the one or more sources of protein comprise whey protein concentrate, whey protein isolates, and/or whey protein hydrolysates;
wherein:
the whey protein concentrate, whey protein isolates, and/or whey protein hydrolysates comprise β-lactoglobulin in an amount sufficient to provide a molar ratio of EGCg to β-lactoglobulin of 1:1 to 11:1 in the composition prior to sterilization,
the pH of the liquid nutritional composition is in a range of from 2.5 to 4.6,
the liquid nutritional composition contains no more than 340 mg/L of gallocatechin gallate (GCg);
the liquid nutritional composition has been heat sterilized and is clear after sterilization; and
the liquid nutritional composition comprises a β-lactoglobulin-EGCg complex that reduces oxidation of the EGCg and reduces hydrolyzation of the EGCg by gastric pepsin.

* * * * *